United States Patent [19]
Bruhn

[11] Patent Number: 6,138,676
[45] Date of Patent: Oct. 31, 2000

[54] COVERING SYSTEM FOR OPERATION PATIENTS

[75] Inventor: Esben Bruhn, Odder, Denmark

[73] Assignee: Surcon A/S, Odder, Denmark

[21] Appl. No.: 09/147,042

[22] PCT Filed: Mar. 25, 1997

[86] PCT No.: PCT/DK97/00132

§ 371 Date: Sep. 23, 1998

§ 102(e) Date: Sep. 23, 1998

[87] PCT Pub. No.: WO97/35530

PCT Pub. Date: Oct. 2, 1997

[30]    Foreign Application Priority Data

Mar. 25, 1996 [DK] Denmark ................................ 0340/96
Nov. 19, 1996 [DK] Denmark ................................ 1312/96

[51] Int. Cl.[7] ............................................... A61B 19/00
[52] U.S. Cl. ............................................ 128/849; 128/853
[58] Field of Search ........................................ 128/849–856

[56]    References Cited

U.S. PATENT DOCUMENTS

| | | | |
|---|---|---|---|
| 3,263,680 | 8/1966 | Morgan | 128/853 |
| 5,209,243 | 5/1993 | Glassman | 128/849 |
| 5,546,960 | 8/1996 | Billgren | 128/849 |
| 5,778,890 | 7/1998 | Löfgren | 128/853 |

FOREIGN PATENT DOCUMENTS 2 720 234  12/1995  France .
WO 96/00045  1/1996  WIPO .

*Primary Examiner*—Michael A. Brown
*Attorney, Agent, or Firm*—Nixon Peabody LLP; David S. Safran

[57]    ABSTRACT

For the covering of operation patients it has become customary to use a heat reflecting wrapping sheet for protecting the patients against loss of heat. At the operation area, a hole is cut in this sheet, whereafter the usual, sterile cover sheets (20) are placed around the area (16) and spread over the patient and the table. With the invention it is realised that it is advantageous to combine these sheets, viz. in providing the cover sheets (20) as double layer products with associated, separate and edge connected wrapping sheets (22), whereby the sterile personnel can easily arrange for the required wrapping and at the same time form the opening in the wrapping material with full safety for a correct location thereof. It will then only be required that the wrapping sheets (22) be co-sterilized with the cover sheets.

8 Claims, 3 Drawing Sheets

COVERING SYSTEM FOR OPERATION PATIENTS

The present invention relates to the coverage of patients on the operation table. For more reasons it is desirable to cover these patients with a sterile material, first of all for avoiding a transfer of micro organisms from peripheral, non-sterilized areas of the patient to the disinfected operation area.

Besides, it is desirable to hold the patient covered with a heat insulating cover in order to protect the patient against a noticeable loss of heat during the anaesthesia. For good reasons, such a cover should only be used outside the sterile area, and for this purpose it is known to use a thin plastic sheet with a fine gauze material at one side and with a coating of heat reflecting, on-vapourized aluminium on the other side. The patient may be covered by and more or less wrapped into this material, with the gauze layer facing inwardly for absorbing sweat from the patient. Thereafter a hole can be cut in this sheet, somewhat larger than the operation area, whereafter the abovementioned covering can be established using sterile cover sheets, which are arranged with their free edges located somewhat inside the edge of the hole cut in the heat insulating wrapping. It is customary that the covering sheets are made of a laminate of a plastic sheet and an outer surface coating of a paper web. These sheets, which are not heat reflecting, will not contribute noticeably to the heat insulation, so much less as they are not wrapped about the patient, but should be spread over the top side of the patient and extend therefrom directly to the edges of the operation table and further therefrom down to slightly above the floor.

With the present invention it has been recognized that it is possible to combine these material sheets in order to achieve a facilitating of the handling procedure, viz. in arranging for the operative edge areas of the cover sheets to be directly connected with an underlying sheet of the wrapping material, such that a double layer is provided, in which the metal coated side of the wrapping material faces outwardly towards the smooth inner side of the cover sheet. It is then possible, without any preceding insulation coverage of the patient, to mount the cover sheets in the desired, normal manner for delimitation of the operation area, whereby the two material layers are allowed to extend in common outwardly and downwardly. Thereafter the operator can handle the cover sheets fully as though they were wrapping sheets, i.e guiding them down along the sides of the patient and pushing them, with the fingers, well inwardly under the patient, whereby the double layer is pushed to a folded position, in which the fold is situated underneath the patient and is held in position by the weight of the patient. The insulating wrapping now having been established, what is left is to arrange the the outer cover sheets in the outwardly extending and freely downhanging position. This, however, can be arranged by a simple pulling out of this outer layer from the folded-in area, advantage here being taken of the fact that the two material layers have their respective smooth sides facing each other. The lower or inner layer has its gauze side at the pushed-in fold turned against the patient and the underlying table, respectively, whereby at both sides there will exist a marked frictional engagement which will, without further, enable a separate pulling out of the fold area of the exterior layer, this area being smooth to both sides, and upon this pulling out the exterior layer may then be arranged as desired, while the interior layer remains in its close contact with the patient and even with the underside of the patient.

Optionally, also the cover sheet members may be metallized on their smooth side, whereby it is possible to use the same kind of material for the two layers, and whereby the cover sheets will provide for a modest, yet increased contribution to the heat insulating effect. It should be emphasized that in principle the invention is not bound to any specific material choice, but of course suitable materials should be selected for the different purposes.

For the invention it is an important circumstance that it is now not only the cover sheets, but the total sets of cover and wrapping sheets which should be supplied in sterilized condition. It has been found, however, that a co-sterilization of the wrapping sheets, e.g. by irradiation, will not be connected with noticeable additional costs. Another special circumstance will be that it is the sterile attendants that will handle the wrapping sheets at least in a part of the non-sterile zone; this, however, will be fully acceptable because the sterile wrapping sheets, themselves, form barriers against the relevant non-sterile surfaces.

In the following the invention is described in more detail with reference to the drawing, in which.

Figure 1:
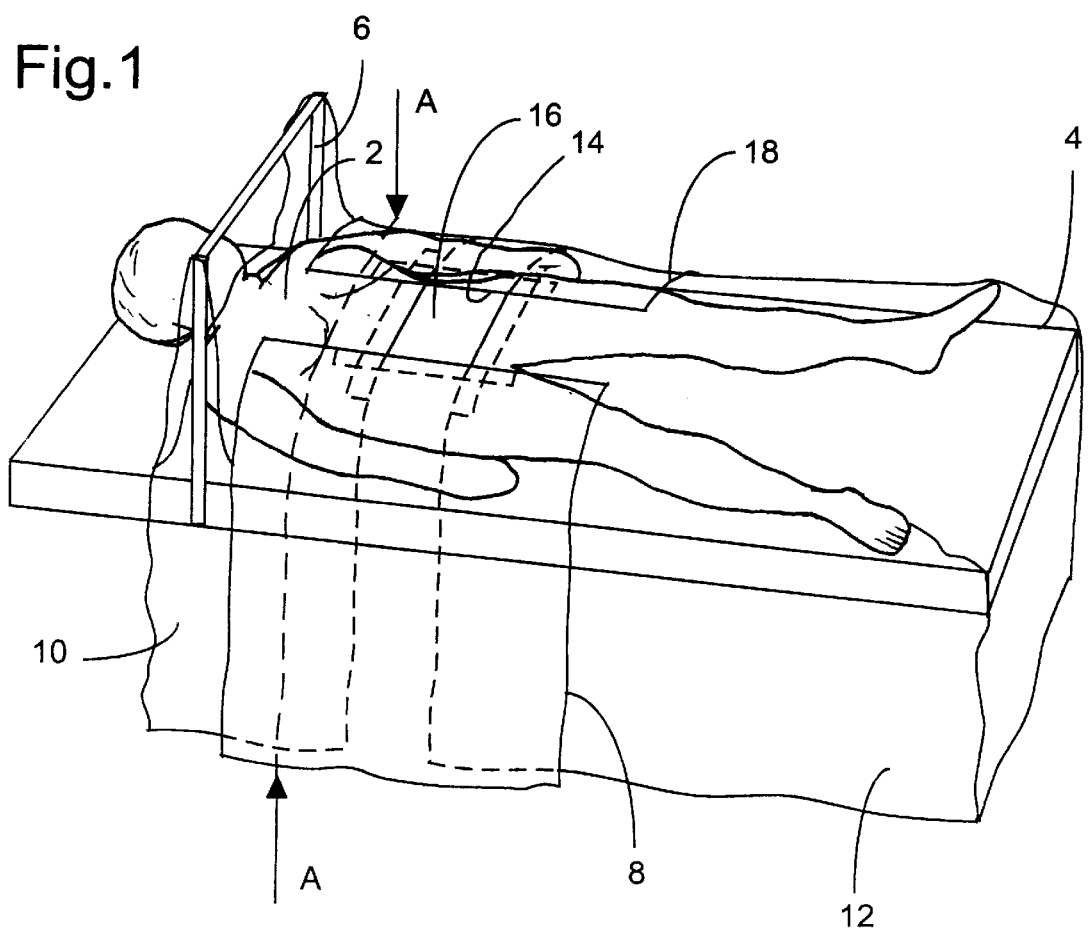
FIG. 1 is a perspective view of an operation patient lying on an operation table.

In FIG. 1 a patient 2 is indicated lying on an operation table 4 with his/her head located behind an upstanding loop 6. Over the patient there are laid out, in a fully usual manner, four cover sheets, viz. two side sheets 8, a top sheet 10 and a bottom sheet 12, the edges 14 of which delimit a rectangular operation area 16, and from which edges the cover sheets extend, respectively, to the sides of the patient and the table and upwardly and downwardly relative to the patient. It is required that these sheets are delivered in sterilized condition, and quite traditionally they consist of a plastic sheet with an absorbing gauze on the top side. At the edges towards the operation area 16 the sheets are made with adhesion areas 18 for adhesion partly to the body of the patient and partly to the sheets mutually, such that a fixedly anchored coverage is provided around the operation area.

Figure 2:
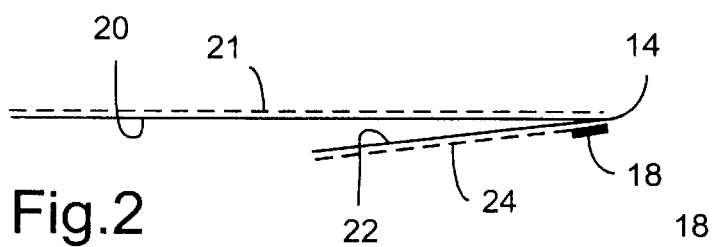
FIG. 2 is an end view of a covering sheet according to the invention.

According to the invention these cover sheets, generally designated 20 in FIG. 2, are, along the edge portions 14, connected with underlying, but otherwise corresponding insulation sheets 22 which, however, have their gauze layer 24 located at the underside, while moreover they are metallized on their top or outer side. The adhesive stripe 18 may thus be located on the inner layer 22,24. The gauze layer on the outer side of the cover sheets is designated 21.

Figure 3:
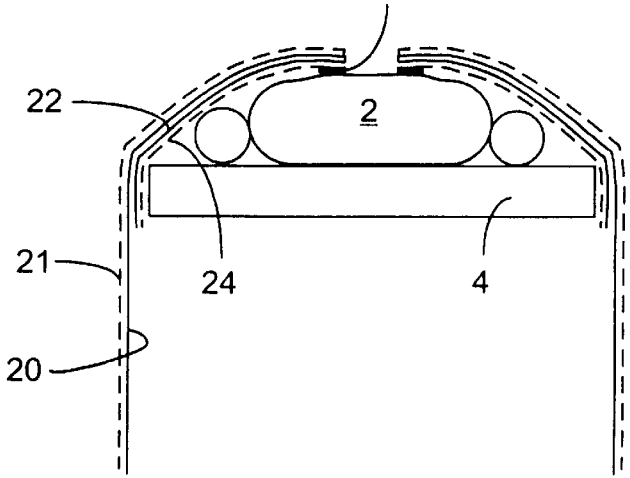
FIGS. 3–5 are sectional views illustrating the invention.

According to FIG. 3, after removal from a sterile package the relevant double layer sheets may be laid onto the patient in the same manner as the cover sheets alone have usually been laid out, after preceding disinfection of the operation area 16 or rather an area somewhat bigger than that. The adhesion areas 18 are fixed by pressing them against the borders of the operation area, and the sheet members 20,22 are draped out over the patient and the table edges.

Figure 4:
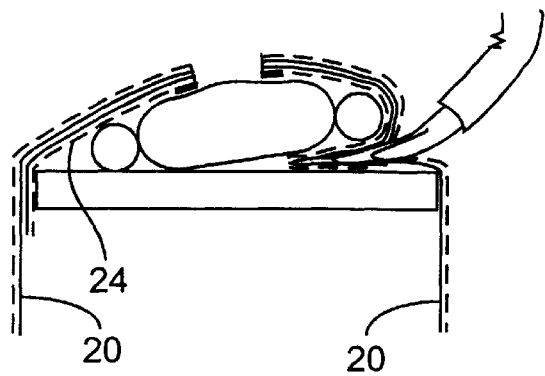
Figure 5:
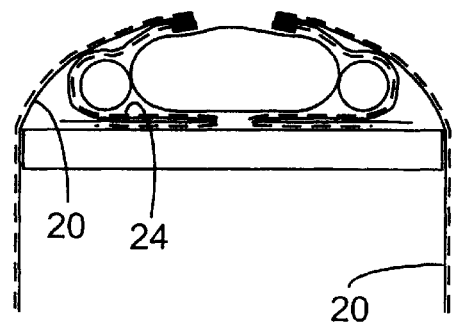

As shown in FIG. 4, the operator can then, with the fingers, push the double layer sheets inwardly under the patient, whereby the inner layer 22,24 will be brought to a fixed position relatively to the patient, while thereafter it is possible to freely draw out the outer layer 20, as the inner smooth surface thereof will not present any noticeable friction against the outer layer on the inner sheet. Thereafter the outer sheet can be arranged as desired, viz. as shown in FIG. 5, while the inner sheet will remain in its effectively patient insulating position according to the same Figure.

The special covering and insulation sheet sets according to the invention should be delivered in fully sterilized condition, just as conventionally for the outer cover sheets, and they should be handled by the sterile operation staff. It will be noted that it is this staff that carries out the insulation wrapping, inasfar as it is fully acceptable that the sterile hands are moved into the non-sterile area underneath the patient when the sterile sheets form intermediate layers.

Figure 6:
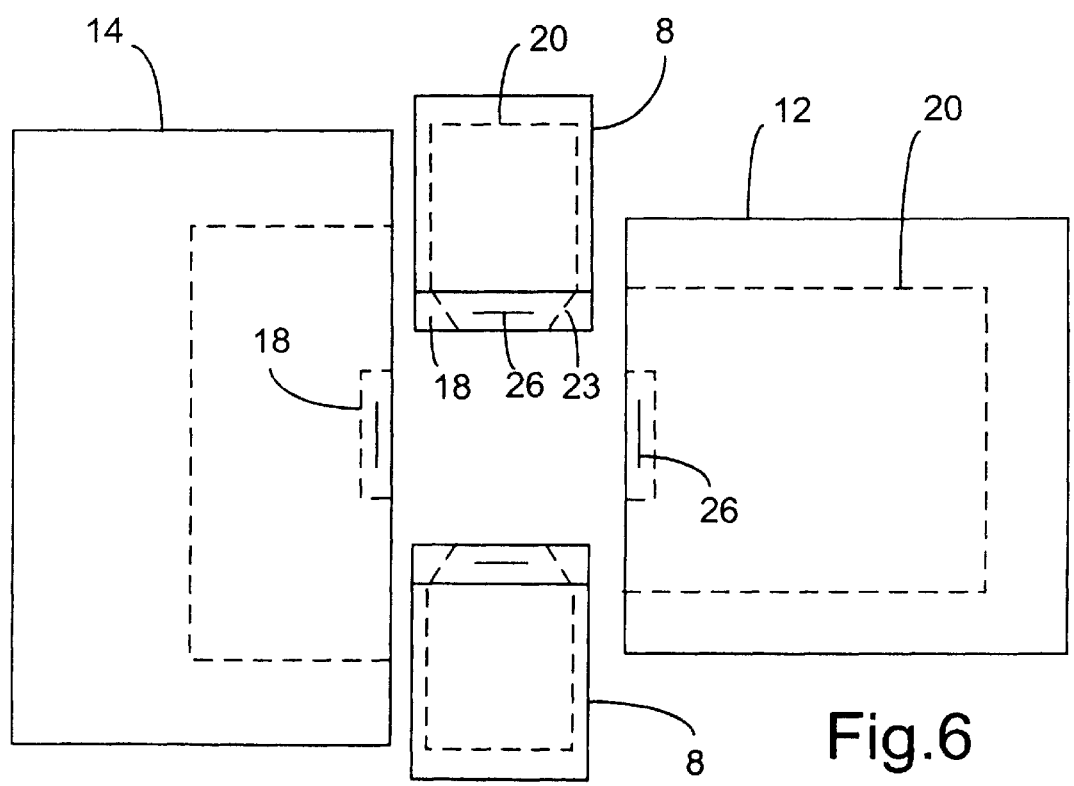
FIGS. 6 and 7 are plan views of a complete set of covering sheets according to the invention, illustrated in respective free and mounted conditions.

In FIG. 6 it is shown in more detail how the four cover sheet units in a complete cover set can be arranged with respect to the distribution of the outer cover material 20 and the inner wrapping material 22,24, shown in dotted lines. With respect to dimensions it may be preferable to distinguish between the two opposed side pieces 8 and the mutually opposed foot and head pieces 12 and 10, respectively, though the invention not being correspondingly restricted. As mentioned, the outer sheets 20 should stretch down to the floor, while the inner sheets 22 should only be packed under the patient, whereby the inner sheets 22 of the end pieces 10 and 12 may be made with smaller dimensions than the outer sheets 2, both width- and lengthwise. The inner sheets 22 should be edge joined with the outer sheets 20 along a central stretch 26, but otherwise exhibit freely projecting side portions which can be wrapped underneath the side of the patient while the free end portion of the outer sheet 20 can be drawn to the floor. It may be preferred to renounce a folding in of the insulation sheet 4 underneath the head and foot ends of the patient, as it may be considered sufficient to rely on the lateral wrapping.

Thus, the conditions for the side pieces 8 may be different, as these may well be connected with the inner sheets 22 all over their width or a large part of it. In principle, the two layers may be uniform, and in that case the double layer product may be a single, simply folded and partly folding edge cut sheet member.

The two layers of each double layer unit should not necessarily be joined along a free edge portion. Thus, if it is desired that just around the operation area there should be an edge area of the outer layer with but a single layer thickness, then the inner layer may be welded or tape connected to the outer layer spaced e.g. a few cm from the free edge of the outer layer, whereby the adhesive layer 18, which may also consist of an added, double sided adhesive tape, may optionally appear solely at a projecting outer edge area of the outer cover sheet 20.

Figure 7:
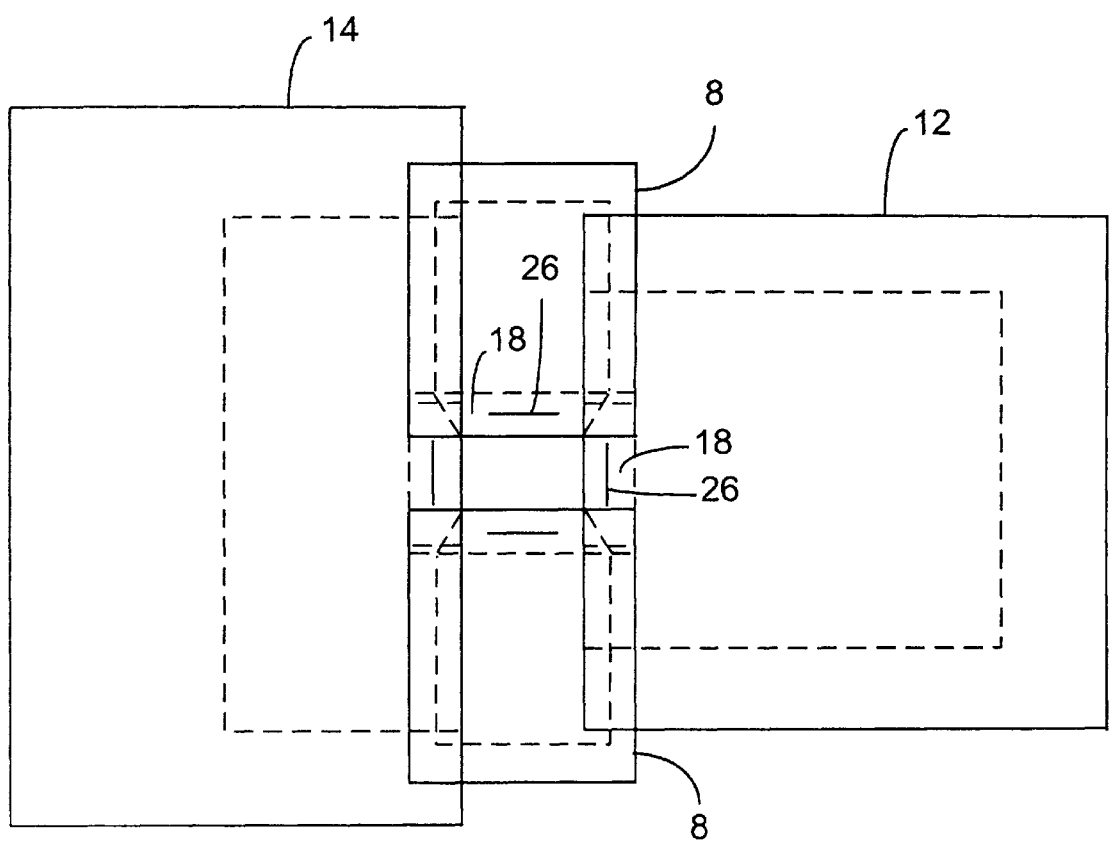

FIG. 7 shows the mutual positioning of the cover sheet members as placed on a patient. It should be mentioned that the side pieces 8 in a preferred embodiment have a width of approximately 75 cm, whereby the preferred measurements can be determined based on this Figure. The invention, however, is not limited to certain sizes or mutual size relations of the involved sheets.

It will be noted that the wrapping sheets 22 will generally be smaller than the cover sheets 20, so they will not be dominating in the product units that should be prepared for distribution in fully sterilized packages. In its folded together condition the whole set will not take up much space in a welding closed packing bag.

It does not appear from FIG. 7 which of the overlapping double sheets are the upper and the lower, respectively; it is not required to prescribe any special arrangement in this respect.

What is claimed is:

1. A covering system for operation patients, comprising a number of sterilized cover sheets to be laid over the patient and the table and to be edge connected with the patient about an exposed operation area, the system also comprising a heat insulating wrapping sheet for near body coverage of the patient outside the operation area by being wrapped about part of the patient, characterized in that the wrapping sheet is comprised of a plurality of wrapping sheet pieces, each piece being edge joined with a respective one of the said cover sheets along at least a partial length of the edge thereof which serves to delimit the operation area, forming double layer units of cover sheets and wrapping sheets, the double layer units of cover sheets and wrapping sheets, single or in groups, being packed in packings in sterilized condition.

2. A covering system according to claim 1, in which the cover sheet and the wrapping sheet of each double layer unit are made with interfacing surfaces with low mutual friction, preferably in the form of metallized plastic sheet surfaces.

3. A covering system according to claim 1, in which the cover sheets, which are made of plastics with a gauze coating on the upper or outer side, are also provided with a metallic coating on the lower or inner side.

4. A covering system according to claim 1, in which the wrapping sheets are made of plastics with a gauze coating at the inner side and a metallic coating at the outside.

5. A covering system according to claim 1, in which the wrapping sheets are smaller than the cover sheets in the length and/or width direction thereof and are mounted substantially symmetrically about the longitudinal middle axis of the cover sheets.

6. A covering system according to claim 1, in which the wrapping sheets and the cover sheets are joined along a relatively short partial edge length at a middle area of the common edge.

7. A covering system according to claim 6, in which the joining area is located inside an adhering edge strip area which is provided on the free side of the cover sheet adjacent at least a middle area of the common edge.

8. A covering system according to claim 1, in which the cover sheet is fixed to the wrapping sheet slightly retracted from the edge thereof.

* * * * *